(12) United States Patent
Nebolsin et al.

(10) Patent No.: US 9,605,013 B2
(45) Date of Patent: Mar. 28, 2017

(54) DERIVATIVES OF HEMIN WITH ANTIBACTERIAL AND ANTIVIRAL ACTIVITY

(71) Applicant: OBSCHESTVO S OGRANICHENNOI OTVETSTVENNOSTIYU "PHARMENTERPRISES", Moscow (RU)

(72) Inventors: Vladimir Evgenievich Nebolsin, Moscow (RU); Galina Alexandrovna Zheltukhina, Moscow (RU); Sergei Alexandrovich Okorochenkov, Sevastopol (RU)

(73) Assignee: OBSCHESTVO S OGRANICHENNOI OTVETSTVENNOSTIYU "PHARMENTERPRISES", Moscow (RU)

( * ) Notice: Subject to any disclaimer, the term of this patent is extended or adjusted under 35 U.S.C. 154(b) by 170 days.

(21) Appl. No.: 14/358,998

(22) PCT Filed: Nov. 15, 2012

(86) PCT No.: PCT/RU2012/000939
§ 371 (c)(1),
(2) Date: Sep. 30, 2014

(87) PCT Pub. No.: WO2013/073998
PCT Pub. Date: May 23, 2013

(65) Prior Publication Data
US 2015/0031854 A1   Jan. 29, 2015

(30) Foreign Application Priority Data

Nov. 17, 2011  (RU) .............................. 2011146831

(51) Int. Cl.
| | | |
|---|---|---|
| *C07D 487/22* | (2006.01) | |
| *C07K 14/795* | (2006.01) | |
| *A61K 31/555* | (2006.01) | |
| *A61K 38/00* | (2006.01) | |
| *C07F 15/02* | (2006.01) | |
| *C07K 5/062* | (2006.01) | |
| *C07K 5/072* | (2006.01) | |

(52) U.S. Cl.
CPC .......... *C07F 15/025* (2013.01); *A61K 31/555* (2013.01); *C07D 487/22* (2013.01); *C07K 5/06069* (2013.01); *C07K 5/06095* (2013.01); *C07K 5/06104* (2013.01); *C07K 14/795* (2013.01); *A61K 38/00* (2013.01)

(58) Field of Classification Search
CPC .............. C07F 15/025; C07K 5/06104; C07K 5/06069; C07K 5/06095; C07K 14/795; C07K 487/22; A61K 31/555
See application file for complete search history.

(56) References Cited

U.S. PATENT DOCUMENTS

2012/0264724 A1   10/2012   Nebolsin et al.

FOREIGN PATENT DOCUMENTS

| RU | 2238950 C2 | 10/2004 |
|---|---|---|
| RU | 2250906 C2 | 4/2005 |
| RU | 2280649 * | 6/2006 |
| RU | 2296131 C2 | 3/2007 |
| RU | 2404191 C2 | 11/2010 |
| WO | 92/02242 A1 | 2/1992 |
| WO | 2011/031187 A1 | 3/2011 |
| WO | 2011031187 A1 | 3/2011 |

OTHER PUBLICATIONS

Kwitniewski et al. In. J. Cancer: 125, 1721-1727(2009).*
International Search Report mailed May 7, 2013 in counterpart International Application No. PCT/RU2012/000939.
Y. Nitzan, H. Ladan, S. Gozansky, and Z. Malik "Characterization of Hemin Antibacterial Action on *Staphylococcus aureus*" FEMS Microbiol. Lett., 1987, vol. 48(3), pp. 401-406.

(Continued)

*Primary Examiner* — Valerie Rodriguez-Garcia
(74) *Attorney, Agent, or Firm* — Banner & Witcoff, Ltd.

(57) ABSTRACT

The invention relates to hemin derivatives of general formula (I), preparing and use thereof as antibacterial and/or antiviral agents, including, as a component in a pharmaceutical compositions. Advantages of the antibacterial and antiviral agents based on the hemin derivatives are in their biocompatibility, biodegradability, a high efficacy against resistant bacteria and widespread viruses which are dangerous to humans, and the lack of toxicity.

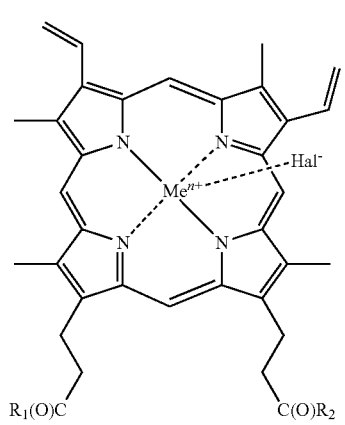

14 Claims, 1 Drawing Sheet

(56) References Cited

OTHER PUBLICATIONS

Database CA [online]; Estigneeva, R.P. et al."Solid-phase synthesis of conjugates of oligopeptides with hemin and their effect on HIV-1 proteinase": received from STN, database accession No. 2002:110489.
Ryabova, Ekaterina S. et al: Journal of Biological Inorganic Chemistry, vol. 9, pp. 385-395, 2004.
Igor Stojiljkovic et al: Expert Opinion on Investigational Drugs, vol. 10, No. 2, pp. 309-320, Feb. 2001.
Nitzan Y et al: Fems Microbiology Letters, vol. 48, No. 3, pp. 401-406, Dec. 1987.
Tsutsui K et al: Biochemical and Biophysical Research Communications, vol. 149, No. 2, pp. 628-634, Dec. 1987.
Apr. 14, 2015—(EP) Supplementary European Search Report—App 12 850 312.

* cited by examiner

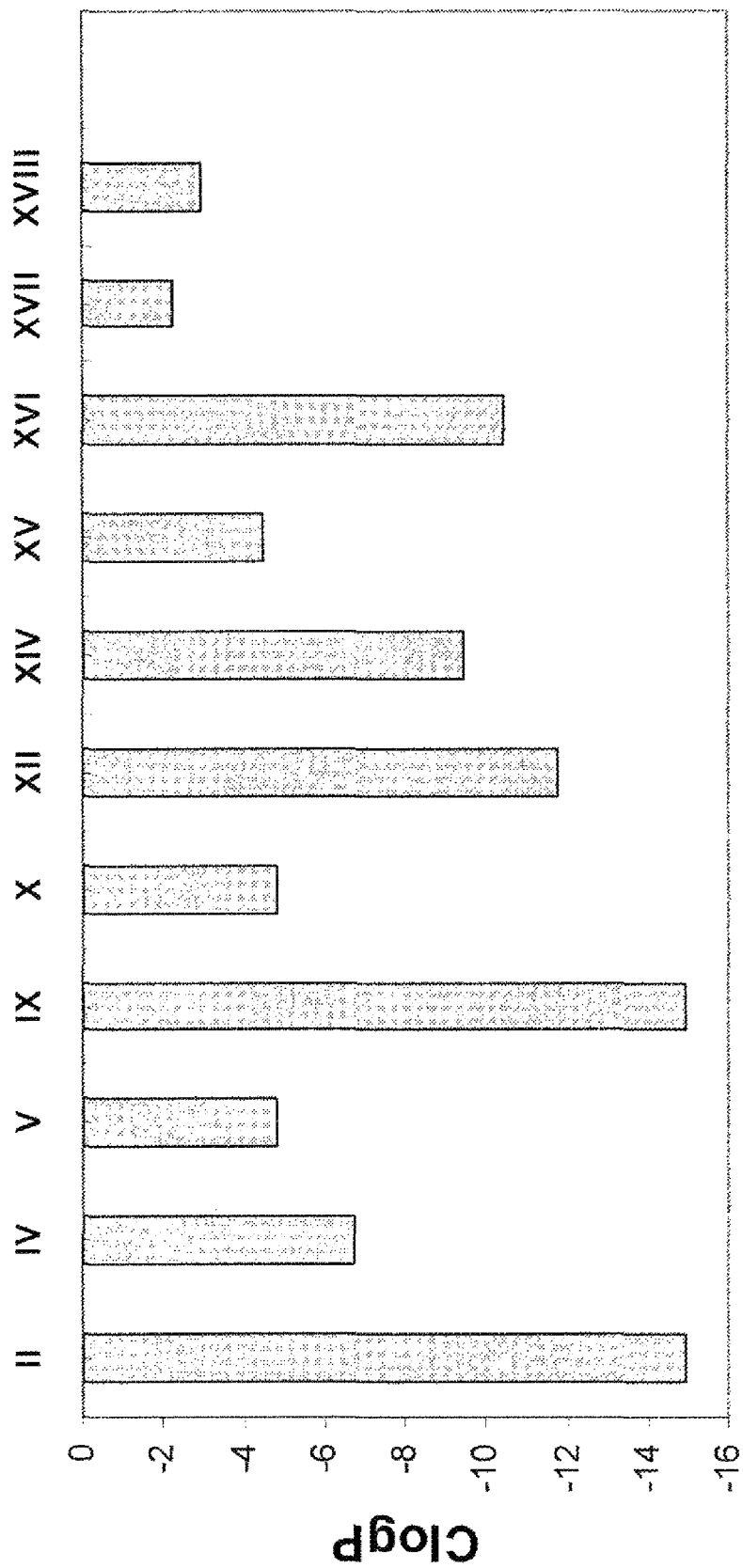

DERIVATIVES OF HEMIN WITH ANTIBACTERIAL AND ANTIVIRAL ACTIVITY

CROSS-REFERENCE TO RELATED APPLICATIONS

This application is a U.S. National Stage application under 35 U.S.C. §371 of International Application PCT/RU2012/000939 (published as WO 2013/073998 A1), filed Nov. 15, 2012, which claims priority to Application RU 2011146831, filed Nov. 17, 2011. Benefit of the filing date of each of these prior applications is hereby claimed. Each of these prior applications is hereby incorporated by reference in its entirety.

TECHNICAL FIELD

The invention relates to the field of bioorganic chemistry and is directed to the obtaining of novel hemin derivatives and to the development of antibacterial and antiviral agents and compositions based thereon.

BACKGROUND

Many dangerous diseases in humans and animals are known to be caused by bacteria and viruses. Bacteria cause such epidemic diseases as cholera, typhoid fever, paratyphoid fever, plague, diphtheria, tularemia, brucellosis, as well as tuberculosis, septicemia (blood poisoning), leprosy, syphilis, and others. In animals, bacteria cause equinia, anthrax, tuberculosis, and other diseases. Strategy in the fight against microorganisms involves the administration of antibacterial agents, including antibiotics. However, many known agents suffer from drawbacks such as toxicity, sensitivity to proteolytic enzymes, a hemolytic effect, and an insufficient range of antibacterial activity. Consistent development of resistant strains, i.e. strains resistant to known antibacterial agents, is a serious problem. Thus at the moment, for example, methicillin-resistant *staphylococcus* (MRSA) which is resistant to a large group of beta-lactam antibiotics currently is most dangerous. Methicillin-resistant *staphylococcus* causes difficult-to-treat diseases in humans such as blood diseases and pneumonia. It has adapted to methicillin, difloxacin, and oxacillin. This pathogen is often associated with nosocomial infections. Each year more than 18,000 American patients die from methicillin-resistant *staphylococcus* infections.

In this context, a search for novel antibacterial agents, including those that are active against resistant strains is still of great interest.

Viruses also cause different diseases, such as influenza, acute respiratory viral infection (ARVI), viral hepatitis, etc. Herpes Simplex viruses are the most known representatives of herpesviruses (the family Herpesviridae) since they infect almost every person. There are two types of herpes simplex viruses (HSV)—HSV-1 (oral herpes) and HSV-2 (genital herpes). Herpes viruses can affect the nervous system, eyes and internal organs. Herpes virus is the most common cause of acute viral encephalitis in the U.S. Herpes Simplex virus type 1 is a causative agent in more than 95% of herpes encephalitis cases. Acyclovir is a well-known agent against herpes viruses. However, since acyclovir-resistant herpes virus strains already exist, a search for novel anti-herpetic agents is still of current interest.

Hemin is known to have an antimicrobial activity against *Staphylococcus aureus* [Y. Nitzan, H. Ladan, S. Gozansky, and Z. Malik, "Characterization of Hemin Antibacterial Action on *Staphylococcus aureus*," FEMS Microbiol. Lett., 1987, Vol. 48(3), pp. 401-406]. However, the use of hemin as an antibacterial agent is hampered by its water insolubility, hemolytic activity, and short-term antibacterial effect.

Efforts were undertaken to modify hemin by the conjugation thereof with amino acids, peptides and derivatives thereof to produce biologically active derivatives. The modification of the hemin carboxy groups to prepare the corresponding amides resulted in compounds, which were studied, of general formula (I)

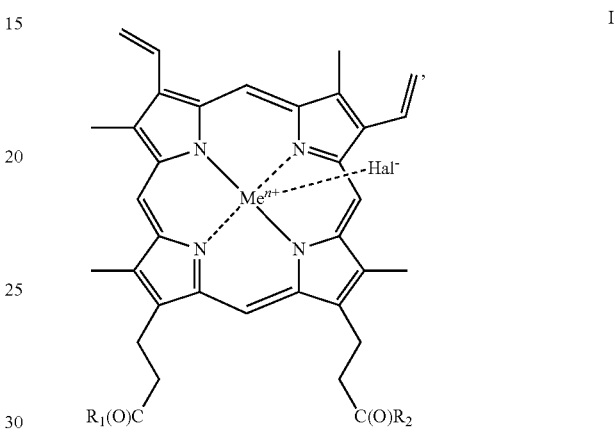

wherein $R_1$ and $R_2$, are the same or different, representing —OH or an amino acid or peptide moiety, and wherein $R_1$ and $R_2$ cannot simultaneously be —OH. $Me^{n+}$ is $Fe^{2+}$ or $Fe^{3+}$; $Hal^-$ is $F^-$, $Cl^-$, $Br^-$ or $I^-$, [RU patent No. 2250906, published on Apr. 27, 2005]. These derivatives have been found to manifest various biological activities, including nuclease [RU patent No. 2404191, published on Nov. 20, 2010], [RU patent No. 2250906, published on Apr. 27, 2005], peroxidase, catalytic [RU patent No. 2404191, published on Nov. 20, 2010], and virulicide activities [RU patent No. 2404191, published on Nov. 20, 2010].

Among the hemin derivatives that have been synthesized earlier by the present inventors there are a number of specific compounds exhibiting an antimicrobial (including antibacterial) activity [RU patent No. 2415868 C1, published on Apr. 10, 2011]. These compounds mainly represent conjugates of hemin with amino acid esters and antimicrobial peptides, where hemin derivatives wherein in particular, $R_1=R_2=$-GlyOMe, $R_1=R_2=$—NHCH$_2$CH$_2$OH, SerOMe or -Glu(ArgOMe)-ArgOMe, have been found to possess antibacterial activity. However, only a few number of hemin derivatives were found to be effective against resistant bacterial strains, which derivatives are also hardly soluble in water and have a lower activity.

At the moment, novel hemin derivatives have been found, which demonstrate antibacterial and antiviral activities and have improved properties, in particular, possess activity against MRSA strains.

SUMMARY OF THE INVENTION

The present invention relates to novel hemin derivatives of general formula (I)

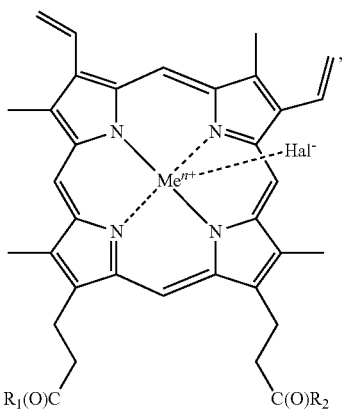

wherein $R_1$ and $R_2$ are both $ArgNH_2$, $Arg(NO_2)OMe$, $GlyNH_2$, $SerNH_2$, $SerOH$, $GlyOH$, $Glu(OH)OH$, $Glu(ArgNH_2)ArgNH_2$, $Glu(SerOMe)SerOMe$, $Glu(NHCH_2CH_2OH)NHCH_2CH_2OH$, $Glu(SerNH_2)SerNH_2$, $Glu(GlyNH_2)GlyNH_2$, $Glu(GlyOMe)GlyOMe$, Arg-SerOMe, ArgSerNH₂, ArgSerOH, SerArgOMe, SerArgNH₂, or SerArgOH, $Me^{n+}$ is $Fe^{2+}$ or $Fe^{3+}$; Hal⁻ is F⁻, Cl⁻, Br⁻ or I⁻, or a pharmaceutically acceptable salt thereof.

In addition, the invention relates to a pharmaceutical composition based on the aforesaid compounds and the use of these compounds in the manufacture of medicaments with antibacterial and/or antiviral activity.

BRIEF DESCRIPTION OF THE DRAWINGS

FIG. 1 shows a comparison of C Log P of the claimed and known compounds of general formula (I).

DETAILED DESCRIPTION OF THE INVENTION

The present inventors have found that the novel compounds of the above general formula (I) are more effective than earlier known analogs.

Advantages of the novel hemin derivatives of general formula (I) are their high water solubility and high antibacterial efficacy, against resistant strains as well.

The claimed novel compounds differ from the earlier known ones by their activity against dangerous resistant strains of gram-positive bacteria St. aureus No. 5 and MRSA St. aureus No. 3797 MRSA and gram-negative E. coli 4300. It has been unexpectedly found that hemin derivatives of general formula (I) with an unprotected carboxyl group or the corresponding amide as a substituents exhibit higher antibacterial activity. Thus, under the same conditions, compounds II, IV, and X exhibit higher antibacterial activity than their corresponding esters disclosed in RU patent No. 2415868C1, published on Apr. 10, 2011.

At the same time, the toxicity of the novel compounds remains low. It should be noted that the compounds comprising an amidated carboxyl group have a higher solubility in water than their analogs comprising a carboxyl or ester group. It seems to be due to higher hydrophilicity of the substituents of these compounds, which is characterized by the octanol-water partition coefficient.

The following novel compounds of formula (I) have been obtained and tested herein:

Compound (II): $R_1=R_2=-ArgNH_2$;
Compound (III): $R_1=R_2=-Arg(NO_2)OMe$;
Compound (IV): $R_1=R_2=-GlyNH_2$;
Compound (V): $R_1=R_2=-SerNH_2$;
Compound (VI): $R_1=R_2=-SerOH$;
Compound (VII): $R_1=R_2=-GlyOH$;
Compound (VIII): $R_1=R_2=-Glu(OH)OH$;
Compound (IX): $R_1=R_2=-Glu(ArgNH_2)ArgNH_2$;
Compound (X): $R_1=R_2=-Glu(SerOMe)SerOMe$;
Compound (XI): $R_1=R_2=-Glu(NHCH_2CH_2OH)NHCH_2CH_2OH$;
Compound (XII): $R_1=R_2=-Glu(SerNH_2)SerNH_2$;
Compound (XIII): $R_1=R_2=-Glu(GlyNH_2)GlyNH_2$;
Compound (XIV): $R_1=R_2=-Glu(GlyOMe)GlyOMe$;
Compound (XIX): $R_1=R_2=-ArgSerOMe$;
Compound (XX): $R_1=R_2=-ArgSerNH_2$;
Compound (XXI): $R_1=R_2=-SerArgOMe$:
Compound (XXII): $R_1=R_2=-ArgSerOH$;
Compound (XXIII): $R_1=R_2=-SerArgNH_2$;
Compound (XXIV): $R_1=R_2=-SerArgOH$.

All amino acids in the hemin derivatives are L-amino acids unless otherwise indicated.

Dipeptides comprising the sequence ArgSer are known compounds. Thus, CAS numbers of ArgSerOMe, ArgSerNH₂ and ArgSerOH are 147139-57-9, 121185-78-2, and 70921-62-9, respectively. Dipeptides SerArgNH₂ and SerArgOH are also known: CAS 1008793-14-3 and 13261-11-5, respectively. The protected dipeptide derivative Boc-Ser(Bzl)ArgOH, CAS 88263-54-1 was also described earlier. The other protected dipeptide derivatives Z₃ArgSerOMe, Z₃ArgSerNH₂, Z₃ArgSerOH, BocSer(Bzl)ArgOMe, BocSer(Bzl)ArgNH₂, and dipeptide SerArgOMe used herein as intermediates to prepare hemin derivatives are novel. These peptides were synthesized by the methods of peptide chemistry, in particular, by the method of activated N-oxysuccinimide esters. Benzyloxycarbonyl (Z) and benzyl (Bzl) protecting groups were cleaved by hydrolysis in the presence of a palladium catalyst, and a tert-butoxycarbonyl (Boc) protecting group was removed with methanol saturated with hydrogen chloride.

The compounds of formula (I) can be used either in the form of salts with pharmaceutically acceptable acids (e.g., lactic, tartaric, citric, hydrochloric, or another acid), or in the form of salts of the carboxyl groups thereof with alkali or alkaline-earth metal ions (such as sodium, potassium, and calcium) or with, for example, pharmaceutically acceptable bases, such as ammonia and ethanolamine.

The above-described compounds of formula (I) are active against bacteria, such as Staphylococcus (e.g., Staphylococcus aureus), Bacillus (e.g., Bacillus subtilis), Enterococcus (e.g., Enterococcus faecalis), Micrococcus (e.g., Micrococcus luteus), and Escherichia (e.g., Escherichia coli) bacterial genera, in particular, against bacteria that are resistant to known antibacterial agents. Preferably, the above-listed bacteria are Bacillus subtilis BKM B-501, Staphylococcus aureus 209P, Enterococcus faecalis BKM B-871, or Micrococcus luteus BKM Ac-2230 strains. Still more preferably, the aforementioned compounds have antibacterial activity against Staphylococcus aureus No. 25923 ATCC, Staphylococcus aureus No. 100 KC, Staphylococcus aureus No. 5 MRSA, Staphylococcus aureus No. 3797 MRSA, Staphylococcus epidermidis No. 533, Enterococcus faecalis No. 559, Enterococcus faecium No. 569, or Escherichia coli 4300.

Furthermore, the compounds according to the invention are active against viruses, in particular, against herpes viruses, such as Herpes Simplex Virus type 1 and/or type 2. Preferably, the compounds according to the invention exhibit activity against Herpes Simplex Virus type 1 strain EC and/or type 2 strain G (No. VR-734 ATCC).

The aforementioned compounds of formula (I) and/or salts thereof can be used as active agents of pharmaceutical compositions (e.g., in solid, semisolid, or liquid forms) formulated with an organic or inorganic carrier or excipient.

The active agent in the composition can be formulated with conventional nontoxic and pharmaceutically acceptable carriers that are suitable for preparing solutions, tablets, pills, capsules, suppositories, emulsions, suspensions, sprays, inhalers, drops, ointments, or any other dosage forms. As a carriers water, glucose, lactose, gum arabic, gelatin, starch, magnesium trixylitol, talc, cornstarch, urea, polyethylene glycol, and other carriers suitable for manufacturing solid, soft, or liquid preparations may be used. Herein, stabilizers, thickeners, coloring agents, and flavoring agents may be used as additives.

A compound of formula (I) is included in the composition in an amount sufficient for providing an antibacterial and/or antiviral effect.

In manufacturing a unit dosage form, the amount of the active agent formulated with a carrier can vary depending on the recipient under therapy and on the particular route of administration of the therapeutic agent.

For example, when compounds of the present invention are used as solutions for injection, the content of the active agent in the solution ranges from 0.001 to 1% by weight. Diluents for the compounds can be 0.9% sodium chloride solution, distilled water, Novocain solution for injections, Ringer's solution, and glucose solution. When compounds of general formula (I) are used as tablets or suppositories, the amount of the compound ranges from 1.0 to 100.0 mg per unit dosage form. For tablets and suppositories, the pharmaceutical excipient can be any pharmaceutically suitable base.

Since the compounds of general formula (I) are both water-soluble and lipophilic, they can be used as aqueous solutions, alcoholic solutions, ointments, creams, etc.

Further, the invention relates to an antibacterial and antiviral therapeutic agent based on the aforementioned compounds of formula (I) and to a method for treating diseases caused by the aforementioned bacteria and/or viruses, the method comprising administering to a patient in need thereof said compound of formula (I) or a pharmaceutical composition thereof.

The method is intended for treating mammal patients, in particular humans. The recommended doses of a compound of formula (I) are from 0.01 to 10 mg/kg.

Since the compounds of formula (I) have antibacterial and antiviral activities, they can likewise be used as (or in) antiseptic and/or disinfectant agents. These agents can be prepared as, for example, solutions with various solvents, such as water and lower alcohols (e.g., 1-propanol or 2-propanol).

Another aspect of the invention relates to a process for preparing the described above novel compounds of formula (I).

Compounds of formula (I) are prepared by reacting a hemin derivative activated at carboxyl groups with an amino component by conventional methods of peptide synthesis.

Amino components can be peptides, amino acids (mostly, α-amino acids), or analogues thereof, in particular, $ArgNH_2$, $Arg(NO_2)OMe$, $GlyNH_2$, $SerNH_2$, $SerOH$, $GlyOH$, $Glu(OH)OH$, $NH_2CH_2CH_2OH$, GlyOMe, and SerOMe, as well as dipeptide derivatives, such as ArgSerOMe, $ArgSerNH_2$, ArgSerOH, SerArgOMe, $SerArgNH_2$ and SerArgOH. The reaction is preferably carried out in the DMF.

Preferably, the amino groups of amino components (e.g., the α-amino groups of carboxylprotected amino acids) are acylated with hemin bis-N-oxysuccinimide ester. The reactions are carried out in DMF for 0.5 to 2 h at a temperature of from −15° to +30° C. by using triethylamine. Similar reactions with unprotected amino acids are carried out in DMF in the presence of triethylamine and up to 10% of water. Furthermore, hemin conjugates with branched peptides are prepared by a direct addition of derivatives a COOH group protected amino acids and peptides, to a hemin conjugate with glutamine acid in the presence of the TBTU coupling agent.

Thus, are novel efficacious antibacterial and antiviral agents based on hemin derivatives are provided. Their advantages consist in biocompatibility, biodegradability, an increased activity against resistant bacterial strains, low toxicity, and the lack of side effects, which renders them promising for use as therapeutic agents.

Further, the invention will be illustrated by examples that are in no means intended to limit the scope thereof.

Notations
HSV-1=Herpes Simplex Virus type 1
HSV-2=Herpes Simplex Virus type 2
IR=infrared spectroscopy
GI=growth inhibition
MBC=minimal bactericidal concentration
MIC=minimal inhibitory concentration
SAA=surface active agents (surfactants)
TLC=thin-layer chromatography
CLF=chloroform
CPE=cytopathogenic effect
A=optical density
Boc=tert-butoxycarbonyl
Bzl=benzyl
DMF=N,N'-dimethylformamide
DMSO=dimethyl sulfoxide
$Et_3N$=triethylamine
MeOH=methanol
MH=Mueller-Hilton medium
MRSA=methicillin-resistant *Staphylococcus aureus*
OMe=methyl ether
PEG=polyethylene glycol
TBTU=2-(1H-benzotriazol-1-yl)-1,1,3,3-tetramethyluronium tetrafluoroborate
$TCID_{50}$=tissue cytopathogenic dose causing 50% cell death in a monolayer
Z=benzyloxycarbonyl The examples below illustrate the claimed invention.

The reagents used were L-amino acids and their derivatives purchased from, except glycine, Bachem (Germany) and Reanal (Hungary); and $Et_3N$ (Fluka, Germany). The intermediates, i.e. protected dipeptides $Z_3ArgSerOMe$, $Z_3ArgSerNH_2$ и $Z_3ArgSerOH$, BocSer(Bzl)ArgOMe, BocSer(Bzl)ArgNH$_2$ and BocSer(Bzl)ArgOH, were prepared by methods of peptide chemistry; their physicochemical characteristics are given in Table 1. All solvents were anhydrous, except for those used for extraction from aqueous solutions. The identity of the prepared compounds was verified by TLC on Kieselgel 60 $F_{254}$ plates (Merck, Germany) in the following systems: (1) chloroform-methanol-acetic acid-water (5:4:0.5:0.5), (2) chloroform-methanol-acetic acid-water (5:4:0.2:0.2), and (3) chloroform-methanol (9:1). Chromatograms were developed with the chlorine-tolidine reagent by fluorescence in the UV.

High-resolution mass spectra were obtained on an Ultraflex (Bruker, Germany) time-of-flight mass spectrometer using matrix-assisted laser desorption/ionization (TOF MALDI); 2,5-dihydroxybenzoic acid matrice was used.

IR spectra were recorded on a Magna 750 (Nicolet, USA) Fourier-transform spectrometer.

Electronic spectra were recorded on a Jasco model UV/VS 7800 (Japan) spectrophotometer.

General Method for Preparing Compounds II-V, XIX-XXIV 0.033 mL (0.266 mmol) of $Et_3N$ was added to a suspension of an amino component (0.26 mmol) in 1.5 mL DMF and stirred at room temperature for 3 min. To the resulting solution, a solution of protohemin IX 6,7-bis-N-oxysuccinimide ester (0.100 g, 0.118 mmol) in 5 mL DMF was added and stirred at room temperature for min. The reaction was monitored by TLC in system (3). The reaction mass was concentrated to 1.0 mL under vacuum. For water-insoluble compounds III, IV and V, 10 mL of 0.01 M hydrochloric acid was added to the concentrated reaction mass, the residue was separated and washed with water to neutral pH. The residue was dried in a desiccator over potassium chloride under reduced pressure for a day. For water-soluble compounds II and XIX-XXIV, 2.55 M hydrochloric acid in methanol was added to reach neutral pH, followed by the addition of 0.01 M hydrochloric acid in a saturated solution of NaCl in water. The residue was separated and dried in a desiccator over potassium chloride under reduced pressure for a day and dissolved in 1 mL anhydrous methanol, and, after filtering undissolved NaCl, purified on a column (20×2 cm) packed with Sephadex LH20 with methanol as an eluent. The fractions containing the target product were combined; the solvent was removed under vacuum. The target product was dried in a desiccator over potassium chloride under reduced pressure for a day.

Example 1

6,7-bis-(Amide $N^\alpha$-Arginyl)-Protohemin (IX) (II)

Yield: 0.1020 g (70%); FT-IR spectrum, ν, $cm^{-1}$, KBr pellet: 1656 (amide I), 1534 (amide II). Mass spectrum (MALDI), m/z: 926 $[M-Cl^-]^+$. Electronic spectrum, DMSO, $\lambda_{max}$, nm, ($\epsilon \cdot 10^{-3}$): 403.8 (92.60), 499.2 (6.3643), 623.6 (1.553).

Example 2

6,7-bis-(Methyl Ester $N^\alpha$—($N^G$-Nitro)Arginyl)-Protohemin (IX) (III)

Yield: 0.083 g (65%), Rf 0.26 (1), 0.71 (2). FT-IR spectrum, ν, $cm^{-1}$, KBr pellet: 1737 (CO est.), 1648 (amide I), 1539 (amide II). Mass spectrum, m/z: $[M]^+$ 1001 $[M-NO_2-Cl^-]^+$ 956 $[M-2NO_2-Cl^-]^+$. Electronic spectrum, DMSO, $\lambda_{max}$, nm, ($\epsilon \cdot 10^{-3}$): 404 (1.163), 500.2 (0.986), 623.4 (0.540).

Example 3

6,7-bis-(Amide $N^\alpha$-Glycyl)-Protohemin (IX) (IV)

Yield: 0.092 g (68%). FT-IR spectrum, ν, $cm^{-1}$, KBr pellet: 1654 (amide I), 1536 (amide II). Mass spectrum (MALDI), m/z: 728 $[M-Cl^-]^+$. Electronic spectrum, DMSO, $\lambda_{max}$, nm, ($\epsilon \cdot 10^{-3}$): 402.0 (101.2), 504.2 (7.417), 628.6 (4.201).

Example 4

6,7-bis-(Amide $N^\alpha$-Seryl)-Protohemin (IX) (V)

Yield: 0.105 g (72%). FT-IR spectrum, ν, $cm^{-1}$, KBr pellet: 1651 (amide I), 1530 (amide II). Mass spectrum (MALDI), m/z: 788 $[M-Cl^-]^+$. Electronic spectrum, DMSO, $\lambda_{max}$, nm, ($\epsilon \cdot 10^{-3}$): 404.8 (207.12), 499.2 (6.547), 623.4 (3.603).

Example 5

6,7-bis-[(Methyl Ester $N^\alpha$-L-Seryl)-L-Arginyl]-Protohemin (IX) (XIX)

Yield: 30 mg (65%), Rf 0.43 (5). FT-IR spectrum, ν, $cm^{-1}$, KBr pellet: 3338 (NH), 1740 (C=O est.), 1653 (amide I), 1545 (amide II). Mass spectrum (MALDI): $[M-Cl^-]^+$ 1131.5. Electronic spectrum, DMSO, $\lambda_{max}$, nm, ($\epsilon \cdot 10^{-3}$): 401.8 (63), 585 (3.18).

Example 6

6,7-bis-[(Amide $N^\alpha$-L-Seryl)-L-Arginyl]-Protohemin (IX) (XX)

Yield: 27 mg (58%), Rf 0.25 (6). FT-IR spectrum, ν, $cm^{-1}$, KBr pellet: 3388 (NH), 1652 (amide I), 1544 (amide II). Mass spectrum (MALDI): $[M-Cl^-]^+$ 1100. Electronic spectrum, DMSO, $\lambda_{max}$, nm, ($\epsilon \cdot 10^{-3}$): 400.8 (47), 581.6 (3.34).

Example 7

6,7-bis-[(Methyl Ester $N^\alpha$-L-Arginyl)-L-Seryl]-Protohemin (IX) (XXI)

Yield: 22 mg (55%), Rf 0.6 (9). FT-IR spectrum, ν, $cm^{-1}$, KBr pellet: 3326 (NH), 1738 (C=O est.), 1627 (amide I), 1577 (amide II). Mass spectrum (MALDI): $[M-Cl^-]^+$ 1132. Electronic spectrum, DMSO, $\lambda_{max}$, nm, ($\epsilon \cdot 10^{-3}$): 404.8 (61), 495.6 (3.44), 619.6 (1.9).

Example 8

6,7-bis-[($N^\alpha$-L-Seryl)-L-Arginyl]-Protohemin (IX) (XXII)

Yield: 30 mg (65%), Rf 0.18 (5). FT-IR spectrum, ν, $cm^{-1}$, KBr pellet: 3396 (NH), 1645 (amide I), 1550 (amide II). Mass spectrum (MALDI): $[M-Cl^-]^+$ 1102.5. Electronic spectrum, DMSO, $\lambda_{max}$, nm, ($\epsilon \cdot 10^{-3}$): 404 (76), 495 (5.11), 610 (3.1).

Example 9

6,7-bis-[(Amide $N^\alpha$-L-Arginyl)-L-Seryl]-Protohemin (IX) (XXIII)

Yield: 27 mg (58%), Rf 0.3 (9). FT-IR spectrum, ν, $cm^{-1}$, KBr pellet: 3365 (NH), 1655 (amide I), 1542 (amide II).

Mass spectrum (MALDI): [M-Cl⁻]⁺ 1100. Electronic spectrum, DMSO, $\lambda_{max}$, nm, ($\epsilon \cdot 10^{-3}$): 402.2 (65.3), 496.4 (4.0), 618.2 (2.1).

Example 10

6,7-bis-[(N$^\alpha$-L-Arginyl)-L-Seryl]-Protohemin (IX) (XXIV)

Yield: 22 mg (55%), Rf 0.2 (9). FT-IR spectrum, $\nu$, cm$^{-1}$, KBr pellet: 3340 (NH), 1659 (amide I), 1550 (amide II). Mass spectrum (MALDI): [M-Cl⁻]⁺ 1102. Electronic spectrum, DMSO, $\lambda_{max}$, nm, ($\epsilon \cdot 10^{-3}$): 403.8 (146), 498.4 (8.1), 620.4 (4.9).

TABLE 1

Physicochemical characteristics of the protected intermediate dipeptides

| Formula | $R_f$ (No. of chromatographic system) | Mass spectrum [M⁺] |
|---|---|---|
| BocSer(Bzl)ArgOMe | 0.5 (7) | 466 |
| BocSer(Bzl)ArgNH₂ | 0.2 (10) | 452 |
| BocSer(Bzl)ArgOH | 0.2 (11) | 453 |
| Z₃ArgSerNH₂ | 0.29 (4) | 662.7 |
| Z₃ArgSerOH | 0.29 (4) | 663.1 |
| Z₃ArgSerOMe | 0.64 (4) | 677.7 |

A General Method for Preparing Protected Peptides (Table 1)

A solution of a corresponding amino component (0.7 mmol) and triethylamine (0.83 mmol) in a mixture of 2 mL DMF and 0.3 ml water was added to a 0.64 mmol solution of BocSer(Bzl)ONSu or Z₃ArgONSu in 3 mL DMF. The reaction mixture was stirred at room temperature for 1 hour. The solvent was removed under vacuum; the residue was dissolved in 10 mL n-butanol and extracted with 3×10 mL saturated aqueous solution of NaCl. The organic layer was dried over anhydrous sodium sulphate and filtered. The solvent was removed under vacuum, the residue was dried in a desiccator over potassium chloride under reduced pressure, and then dissolved in 1 mL anhydrous methanol, and salts were filtered. The solvent was removed under vacuum. The target compound was if needed purified by re-crystallization or column chromatography on silica gel.

A General Method for Preparing Compounds VI-VIII 0.130 mL (for serine and glycine) or 0.260 mL (for glutamine acid and dihydrochlorides of arginine and gistidine) triethylamine was added to a solution or suspension of an amino acid (0.945 mmol) in 0.5 mL water. The resulting solution was added to hemin 6,7-bis-N-oxysuccinimide ester (100 mg, 0.118 mmol) in 6 ml DMF, and stirred for 30 min. The reaction mass was concentrated under vacuum to 1 ml. For water-insoluble compounds VI-VIII, 10 mL of aqueous hydrochloric acid (0.01M) was added to the concentrated reaction mass; the residue was separated and washed with water up to neutral pH. The residue was dried in a desiccator over potassium chloride under reduced pressure for a day.

Example 11

6,7-bis-(N$^\alpha$-Seryl]-Protohemin (IX) (VI)

Yield: 84.7 mg (87%). FT-IR spectrum (KBr, $\nu_{max}$/cm$^{-1}$): 1727 (COOH), 1656 (C═O amide I), 1530 (C═O amide II). Mass spectrum (MALDI), m/z: 790 [M-Cl⁻]⁺. Electronic spectrum, DMSO, $\lambda_{max}$, nm, ($\epsilon \cdot 10^{-3}$): 403 (188), 497 (8.51), 622 (4.49).

Example 12

6,7-bis-(N$^\alpha$-Glycyl]-Protohemin (IX) (VII)

Yield: 77.7 mg (86%). FT-IR spectrum (KBr, $\nu_{max}$/cm$^{-1}$): 3294 (NH), 1724 (COOH), 1656 (C═O amide I), 1543 (C═O amide II). Mass spectrum (MALDI), m/z: 730.1 [M-Cl⁻]⁺. Electronic spectrum, DMSO, $\lambda_{max}$, nm, ($\epsilon \cdot 10^{-3}$): 404 (126), 498 (8.02), 622 (4.48).

Example 13

6,7-bis-(N$^\alpha$-Glutamyl]-Protohemin (IX) (VIII)

Yield: 88 mg (82%). FT-IR spectrum (KBr, $\nu_{max}$/cm$^{-1}$): 3286 (NH), 172 (COOH), 1644 (C═O amide I), 1544 (C═O amide II). Mass spectrum (MALDI), m/z: 874 [M-Cl⁻]⁺. Electronic spectrum, DMSO, $\lambda_{max}$, nm, ($\epsilon \cdot 10^{-3}$): 404 (76.7), 496 (8.79), 615 (6.02).

A General Method for Preparing Compounds IX-XIV 0.148 g (0.462 mmol) TBTU and 0.086 ml (0.462 mmol) Et₃N were added to 0.070 g (0.077 mmol) 6,7-bis-N$^\alpha$-glutamyl-protohemin (IX) in 5 ml DMF. The resulting solution was stirred for 30 min. To a suspension of 0.462 mmol amino component hydrochloride in 1.5 ml DMF, 0.086 ml (0.462 mmol) Et₃N was added and stirred at room temperature for 3 min, then the resulting solution was added to a solution of pre-activated 6,7-bis-N$^\alpha$-glutamyl-protohemin (IX). The reaction mass was stirred for a day and concentrated to 1.0 mL under vacuum. For water-insoluble compounds (XI and XIV), 10 mL of 0.01 M aqueous hydrochloric acid solution was added to the concentrated reaction mass, the residue was separated and washed with water to neutral pH. The residue was dried in a desiccator over potassium chloride under reduced pressure for a day. For water-soluble compounds (IX, X and XIII), 0.01 M hydrochloric acid in a saturated solution of NaCl in water was added to the concentrated reaction mass. The residue was separated and dried in a desiccator over potassium chloride under reduced pressure for a day and dissolved in 1 mL anhydrous methanol, and, after filtering undissolved NaCl, purified on a column (20×2 cm) packed with Sephadex LH20 with methanol as an eluent. The fractions containing the target product were combined; the solvent was removed under vacuum. The target product was dried in a desiccator over potassium chloride under reduced pressure for a day.

Example 14

6,7-bis-[(Diamide N$^\alpha$-L-Arginyl)-L-glutamyl]-Protohemin (IX) (IX)

Yield: 0.082 g (71%). FT-IR spectrum, $\nu$, cm$^{-1}$, KBr pellet: 1658 (amide I), 1541 (amide II). Mass spectrum (MALDI), m/z: 1495 [M-Cl⁻]⁺. Electronic spectrum, DMSO, $\lambda_{max}$, nm, ($\epsilon \cdot 10^{-3}$): 396.8 (137.83), 505.6 (13.404), 623.2 (6.419).

Example 15

6,7-bis-[(Dimethyl Ester N$^\alpha$-L-Seryl)-L-glutamyl]-Protohemin (IX) (X)

Yield: 0.068 g (67%). FT-IR spectrum, $\nu$, cm$^{-1}$, KBr pellet: 1747 (CO est.), 1646 (amide I), 1542 (amide II). Mass spectrum (MALDI), m/z: 1313 [M-Cl⁻]⁺. Electronic spectrum, DMSO, $\lambda_{max}$, nm, ($\epsilon \cdot 10^{-3}$): 404.6 (124.25), 500 (7.434), 622.2 (4.032).

Example 16

6,7-bis-[(Di-2-hydroxyethylamide)-L-glutamyl]-Protohemin (IX) (XI)

Yield: 0.054 g (64%). FT-IR spectrum, ν, cm⁻¹, KBr pellet: 1654 (amide I), 1547 (amide II). Mass spectrum (MALDI), m/z: 1046 [M-Cl⁻]⁺. Electronic spectrum, DMSO, $\lambda_{max}$, nm, ($\epsilon \cdot 10^{-3}$): 403.2 (107.83), 502.3 (9.041), 635.2 (6.591).

Example 17

6,7-bis-[(Diamide N^α-L-Seryl)-L-glutamyl]-Protohemin (IX) (XII)

Yield: 0.074 g (76%). FT-IR spectrum, ν, cm⁻¹, KBr pellet: 1651 (amide I), 1537 (amide II). Mass spectrum (MALDI), m/z: 1218 [M-Cl⁻]⁺. Electronic spectrum, DMSO, $\lambda_{max}$, nm, ($\epsilon \cdot 10^{-3}$): 398.6 (89.41), 497.4 (4.162), 619.4 (2.124).

Example 18

6,7-bis-[(Diamide N^α-L-Glycyl)-L-glutamyl]-Protohemin (IX) (XIII)

Yield: 0.077 g (87%). FT-IR spectrum, ν, cm⁻¹, KBr pellet: 1652 (amide I), 1539 (amide II). Mass spectrum (MALDI), m/z: 1098 [M-Cl⁻]⁺. Electronic spectrum, DMSO, $\lambda_{max}$, nm, ($\epsilon \cdot 10^{-3}$): 404.4 (88.0), 497.8 (5.184), 621.8 (2.728).

Example 19

6,7-bis-[(Dimethyl Ester N^α-L-Glycyl)-L-glutamyl]-Protohemin (IX) (XIV)

Yield: 0.072 g (78%). FT-IR spectrum, ν, cm⁻¹, KBr pellet: 1738 (CO est.), 1652 (amide I), 1535 (amide II). Mass spectrum (MALDI), m/z: 1158 [M-Cl⁻]⁺. Electronic spectrum, DMSO, $\lambda_{max}$, nm, ($\epsilon \cdot 10^{-3}$): 404.4 (88.0), 497.8 (5.184), 621.8 (2.728).

Example 20

Hydrophilicity of Compounds of General Formula (I)

The octanol-water partition coefficients (CLogP) of the claimed compounds of formula (I), in particular compounds I, II, IV, V, IX, X, XII, XIII, XIV and known compounds of general formula I, wherein R₁ and R₂ are ArgOMe (XV), Glu(ArgOMe)ArgOMe (XVI), GlyOMe (XVII), SerOMe (XVIII) [RU patent 2415868 C1, published on Apr. 10, 2011], were calculated by using software ACDLabs 8.0.

As follows from FIG. 1, substitution of the —OMe group with an NH₂-group leads to an improved hydrophilicity of hemin derivatives. Thus, the claimed novel compounds of general formula I have an improved hydrophilicity compared to the known compounds.

Example 21

Antibacterial Activity of Compounds of General Formula I, Including Resistant Bacterial Strains

Example 21.1

The antibacterial activity of the compounds was determined against strains of gram-positive bacteria such as *Staphylococcus aureus* 209P, *Enterococcus faecalis* BKM B-871, *Micrococcus luteus* BKM Ac-2230, *Bacillus subtilis* BKM B-501, and gram-negative bacteria such as *Pseudomonas aeruginosa* PAO1 and *Escherichia coli* KM MGU C-600. BKM strains were acquired from the All-Russia Collection of Microorganisms at the Institute for Biochemistry and Physiology of Microorganisms, Russian Academy of Sciences. Strain *Staphylococcus aureus* 209P was acquired from the Collection of Microorganisms at the Department of microbiology of the Faculty of Biology of Lomonosov Moscow State University, and *Pseudomonas aeruginosa* PAO1 was acquired from the Collection of Microorganisms at the Institute of Bioorganic Chemistry of the Russian Academy of Sciences.

The main parameters characterizing the antibacterial activity are the minimal inhibitory concentration (MIC) and minimal bactericidal concentration (MBC). MIC is the least concentration of a tested compound that completely inhibits the reproduction of bacteria in a liquid medium. MBC is the least concentration that causes the death of all cells.

MIC was quantified by inhibiting culture growth in a liquid medium with serial dilutions of compounds using a modified procedure [Amsterdam, D., 1966. "Susceptibility testing of antimicrobials in liquid media," pp. 52-111. In Loman, V., ed. Antibiotics in laboratory medicine, 4th ed. Williams and Wilkins, Baltimore].

Bacteria were cultured and tested on an MH liquid medium (Mueller-Hinton medium: a dry extract of beef broth, 4 g/L; starch, 1.5 g/L; casein hydrolyzate, 17.5 g/L; Sigma-Fluka Catalog No. 70192) at 37° C., 100% humidity, and under stirring. Cultures (within 4 to 7 passages after thawing) in the exponential growth phase were used for tests.

All tested compounds absorb light at 595 nm, a wavelength used for evaluating bacterial culture growth. Therefore, a correction for absorption was applied in estimating the optical density of bacterial suspensions for each compound with account for its concentration in the well. Bacterial growth inhibition (GI) as percentage after 20 hours of incubating cells with compounds was derived from the optical density (A) measured in every well at a wavelength of 595 nm using the equation:

$$GI_i = [(A_{ct} - A_{c0}) - (A_{it} - A_{i0})] \times 100 / (A_{ct} - A_{c0}), \quad (1)$$

wherein the subscripts have the following meanings: i denotes the well number, c denotes a control well with bacteria whereto the tested compound is not inserted, 0 refers to the measurement taken immediately once the tested compound was inserted to the well, and t refers to the measurement taken 20 hours after the compound was inserted.

The protocol for the determination of experimental antibacterial activity of the tested compounds was as follows. A cryovial with the test strain culture in a medium with 7% DMSO stored in liquid nitrogen, was rapidly defrosted, and 1.5 mL of the fresh MH medium was inoculated with 100 μL of the cell suspension. Cells were grown for one day at 37° C. and stirred on an orbital shaker at 150 rpm. The morphologic features of the strain and the absence of contamination with foreign bacteria were verified by: (a) inoculation on an agarized (15 g/L agar) MH medium and observation of the shape and color of the grown colonies and (b) examination of characteristic morphologic features under a microscope (Mikmed-2, LOMO, Russia) equipped with a 40× objective lens. Further, the bacteria were cultured in 1 mL of the liquid MH medium at 37° C. under stirring. The cells were reseeded every day. Cell cultures were used in tests starting with $3^{rd}$ reseeding and ending with $6^{th}$ one.

For testing, 5 µL of a bacterial suspension in the stationary growth phase was transferred to 1 mL of a sterile MH medium and incubated until the exponential growth phase was attained (3 to 5 h, 37° C., stirring at 150 rpm). To estimate the microorganism concentration, the optical density (A) of the resulting bacterial culture was measured at a wavelength of 595 nm. The value of A=0.2 measured from a 200-µL portion of the cell suspension in a 96-well plate, with a correction for the medium absorption applied, was set to correspond to $4\times10^8$ cells/mL for both strains used. Taking into account the cell concentration measurements, the suspension was diluted with the MH medium to a concentration of from $5\times10^4$ to $1\times10^5$ cells/mL and transferred to a sterile 96-well plate in an amount of 100 µL per well. Then, the cells were added with tested compounds and twofold serial dilutions of these compounds in plate's wells were made. The maximal concentration of a compound in the series was $10^{-4}$ M; the minimal one was $1.6\times10^{-6}$ M. The antibacterial activity studies were performed in two replicas for each compound, and the results were averaged.

The controls used were: 100 µL of an additive-free bacterial culture (four wells); a bacterial culture added with 1% DMSO or water in the same volume as in the wells with the maximal concentration of the tested compounds (four wells); and 100 µL of the sterile MH medium without bacteria and without tested compounds for control of occasional contamination in the plate (four wells).

Immediately once compounds were inserted, $A_{i0}$ was measured in every well, and $A_{c0}$ was measured in control wells using a Uniplan (Picon, Russia) plate photometer (both values were necessary for calculations by equation (1)). The plate was incubated for 20 h at 37° C. and stirred at 150 rpm. Then, $A_{it}$ was measured in every well and $A_{ct}$ in control wells, and bacterial growth inhibition was calculated from equation (1). MIC was determined as the minimal concentration of the tested compound at which growth inhibition was 100%.

In MBC determinations, the medium from wells wherein the tested compound concentration equaled MIC, MIC×2, and MIC×4 was transferred to Petri dishes with an agarized MH medium (15 g/L agar) and uniformly spread over the area of the dish using sterile spatulas. The dishes were incubated for two days. MBC was determined as the least concentration of the tested compound at which colonies were not grown on Petri dishes.

TABLE 2

Antibacterial activity characteristics of compounds of general formula (I) against gram-positive bacteria *Bacillus subtilis* BKM B-501, *Staphylococcus aureus* 209P, *Enterococcus faecalis* BKM B-871, and *Micrococcus luteus* BKM Ac-2230

| | *Bacillus subtilis* BKM B-501 | | *Staphylococcus aureus* 209P | | *Enterococcus faecalis* BKM B-871 | | *Micrococcus luteus* BKM Ac-2230 | |
|---|---|---|---|---|---|---|---|---|
| compound | MIC, µM | MBC, µM | MIC, µM | MBC, µM | MIC, µM | MBC, µM | MIC, µM | MBC, µM |
| II | 0.8 | 0.8 | 1.6 | 6.3 | 6.3 | 12.5 | 0.8 | 0.8 |
| III | 12.5 | H/И | 25 | n/t | n/t | | 1.6 | 6.3 |
| IV | 1.6 | 1.6 | 6.3 | n/t | n/t | n/t | 0.8 | 0.8 |
| V | 1.6 | 1.6 | 3.2 | 12.5 | 3.2 | n/t | 0.8 | 0.8 |
| VI | 12.5 | 25 | 50 | n/t | n/t | | 6.3 | 25 |
| VII | 25 | 25 | 50 | n/t | n/t | | 12.5 | 25 |
| IX | 1.6 | 1.6 | 3.2 | 25 | 25 | 50 | 0.8 | 0.8 |
| X | 50 | n/t | 12.5 | n/t | 50 | n/t | 12.5 | 25 |
| XIV | 6.3 | 25 | 12.5 | n/t | n/t | | 1.6 | 6.3 |
| XV | 3.1 | 3.1 | 50 | 200 | 50 | 400 | 1.6 | 3.2 |
| XVI | 1.6 | >200** | 6.3 | >200** | 12.5 | >200** | 3.1 | 12.5 |
| XVII | 12.5 | 25 | 50 | 50 | 100 | >200** | 1.6 | 6.5 |
| XVIII | 6.3 | 9 | 25 | 200 | 12.5 | 25 | 6.3 | 12.5 |

**MIC is not reached. The value is the maximal used concentration of the compound.
n/t—not tested Comparative compounds in Table 2 are already known compounds of general formula (I), wherein $R_1=R_2=$ArgOMe (XV), Glu(ArgOMe)ArgOMe (XVI), GlyOMe (XVII), SerOMe (XVIII) [RU patent 2415868 C1, Apr. 10, 2011]. Thus, compounds II, III, IV, V, IX, X, and XIV suppress the growth of gram-positive bacteria *S. aureus* within a micromolar concentration range (Table 2). These compounds also exhibit bactericide activity in concentrations up to 25 µM.

*M. luteus* bacteria are highly sensitive to all compounds in submicromolar concentrations (in several cases MIC<0.8 µM).

*E. faecalis* enterococci are (on the average) more resistant to the tested compounds than *M. luteus* micrococci or *S. aureus* staphylococci. Compounds II and V have the highest efficacy against *E. faecalis*: MIC<7 µM.

Actually all tested compounds are active against Gram-positive bacteria *B. subtilis*.

Example 21.2

The specific activity of compounds also was determined against bacteria strains such as *Staphylococcus aureus* No. 25923 ATCC (American Type Culture Collection); *Staphylococcus aureus* No. 100 KC; *Staphylococcus epidermidis* No. 533; *Enterococcus faecalis* No. 559; *Enterococcus faecium* No. 569, *Staphylococcus aureus* No. 5 (MRSA), *Staphylococcus aureus* No. 3797 (MRSA). *Staphylococcus aureus* was cultured on the Trypticase Soy Agar (BBL) commercially available dry medium. *Enterococcus faecalis* was cultured on the Columbia Agar (BBL) commercially available dry medium. These media were sterilized by autoclaving at 121° C. for 15 min. Bacterial inoculum was constant and was 5×10⁵ CFU/ml (10⁵ CFU/0.2 ml). For water-soluble compounds, wells from 2$^{nd}$ through 8$^{th}$ were added with the solvent (water) in an amount of 15 μL per well, then the 1$^{st}$ well was added with 30 μL of the stock solution of the tested compound in water with a concentration of 1×10³ M, and the concentration was adjusted to 0.007×10³ M by serial twofold dilutions. A 10-μL portion was taken from every well, and 190 μL of the bacterial culture (10⁵ CFU) was added per well. For DMSO-soluble compounds, wells from 2$^{nd}$ through 8$^{th}$ were added with the solvent (DMSO) in an amount of 10 μL per well, then the 1$^{st}$ well was added with 20 μL of the stock solution of the tested compound in water with a concentration of 5×10³ M, and the concentration was adjusted to 0.039×10³ M by serial twofold dilutions. A 2-μL portion was taken from each well, and 198 μL of the bacterial culture (10⁵ CFU) was added per well.

The control comprised wells free of tested compounds (culture growth control). In addition, purity control of nutritional media and solvents was used. Plates were incubated in a thermostat at 36° C. for 24 hours.

Culture growth was evaluated visually by comparison of how microorganisms grew in the presence of tested compounds and in the absence of them. MIC was set equal to the last dilution of a tested agent which suppressed bacterial culture growth.

The antibacterial activity demonstrated by claimed compounds against *Enterococcus faecalis* 559 was slightly less.

Pronounced antibacterial activity against Vancomycin-resistant *Enterococcus faecium* 569 was observed for compounds II (MIC=3.12 μM), IV (MIC=50 μM), V (MIC=25 μM), IX (MIC=6.25 μM), and XIX-XXI (MIC=6.25 μM).

Compounds II (MIC=41.6 μM) and IX (MIC=16.6 μM) were active against gram-negative *E. coli* 4300.

Compounds II (MIC=41.6 μM) and IX (MIC=16.6 μM) were active against gram-negative *E. coli*.

TABLE 4

Antibacterial activity characteristics of compounds of general formula I against Methicillin-resistant gram-positive bacteria *Staphylococcus aureus* No. 5, *Staphylococcus aureus* 3797 (MIC, μM)

|      | St. aur No. 5 MRSA | St. aur No. 3797 MRSA |
| --- | --- | --- |
| II | 41 | 50 |
| III | 25 | 25 |
| IV | 3.12 | 3.12 |
| V | 1.56 | 1.56 |
| VI | 0.78 | 0.78 |
| VII | 6.25 | 6.25 |
| XI | 12.5 | 12.5 |
| XIII | 83 | 50 |
| XIV | 3.12 | 2.6 |
| XIX | 1.56 | 1.3 |
| XX | 3.12 | 1.3 |
| XXI | 0.65 | 1.56 |

TABLE 3

Antibacterial activity characteristics of compounds of general formula I against Gram-positive bacteria *Staphylococcus aureus* 25923, *Staphylococcus aureus* 100 KC, *Staphylococcus epidermis* 533, *Enterococcus faecalis* 559, Vancomycin-resistant *Enterococcus faecium* 569, and Gram-negative Vancomycin-resistant bacteria *Escherichia coli* 4300 (MIC, μM)

|      | S. aureus 25923 | S. aureus 100 KC | S. epidermis 533 | E. faecalis 559 | E. faecium 569 | E. coli 4300 |
| --- | --- | --- | --- | --- | --- | --- |
| II | 1.04 | 2.6 | 0.39 | 1.3 | 3.12 | 41.6 |
| IV | 0.39 | 0.39 | 1.56 | 0.39 | 50 | >50.0 |
| V | 0.78 | 0.52 | 1.56 | 25 | 25 | >50.0 |
| VI | 12.5 | 5.21 | 3.12 | >50.0 | >50.0 | >50.0 |
| VII | 2.6 | 12.5 | 6.25 | >50.0 | >50.0 | >50.0 |
| IX | 1.56 | 0.78 | 0.78 | 3.12 | 6.25 | 16.6 |
| XI | 0.39 | >50.0 | 6.25 | 33.3 | >50.0 | >50.0 |
| XIII | 12.5 | 12.5 | 12.5 | 12.5 | >50.0 | >50.0 |
| XIV | 0.39 | 2.6 | 1.04 | 3.12 | >50.0 | >50.0 |
| XIX | 0.65 | 0.78 | 1.3 | 1.3 | 6.25 | >50.0 |
| XX | 1.3 | 0.65 | 1.56 | 1.56 | 6.25 | >50.0 |
| XXI | 0.39 | 0.65 | 0.78 | 1.56 | 6.25 | >50.0 |
| XXII | 1.3 | 0.39 | 1.3 | >50.0 | 5.2 | >50.0 |
| XXIII | >50.0 | >50.0 | >50.0 | >50.0 | >50.0 | >50.0 |
| XXIV | >50.0 | 5.20 | 2.60 | >50.0 | 6.25 | >50.0 |
| XV | 25 | 50 | 25 | 25 | >50 | >50 |
| XVII | 25 | >50 | 25 | 25 | >50 | >50 |

Comparative compounds in Table 3 are already known compounds of general formula (I), wherein $R_1=R_2=$ArgOMe (XV) or GlyOMe (XVII) [RU patent 2415868 C1, published on Apr. 10, 2011].

The novel compounds were effective against Gram-positive bacteria *Staphylococcus aureus* 25923, *Staphylococcus aureus* 100 KC and *Staphylococcus epidermis* 533, wherein the MIC values were not more than 13 μM. Water-solubility and antibacterial activity of some dipeptide derivatives of hemin were higher then those of the other hemin derivatives. Thus antibacterial activity of compound XIX against *Staphylococcus epidermis* 533 was higher by an order of magnitude (MIC=1.3 μM).

TABLE 4-continued

Antibacterial activity characteristics of compounds of general formula I against Methicillin-resistant gram-positive bacteria *Staphylococcus aureus* No. 5, *Staphylococcus aureus* 3797 (MIC, μM)

|      | St. aur No. 5 MRSA | St. aur No. 3797 MRSA |
| --- | --- | --- |
| XXII | 25 | 20.8 |
| XXIII | >50.0 | >50.0 |
| XXIV | 25 | 25 |

As follows from Table 4, the novel compounds have a high antibacterial activity against MSRA strains, wherein MBC ranges from 0.78 to 13 μM.

Example 22

Antiviral Activity of Hemin Derivatives Against Viruses of the Family Herpesviridae Bacteria used in the study were used Herpes Simplex Virus type 1 (the Collection of Microorganisms at the Scientific Research Institute of Virology, strain EC), Herpes Simplex Virus type 2 strain G (No. VR-734 ATCC), and human cytomegalovirus strain AD169 (No. VR-538 ATCC). Herpes Simplex viruses type 1 and type 2 were cultured in Vero cells. The cells were incubated in MEM Eagle growth medium (MEM, BioloT, St-Petersburg, 1.3.3) supplemented with 10% fetal bovine serum (BioloT, St-Petersburg, 1.3.12) in Sanyo MCO-15AC gas-flow thermostat (37° C., 5% $CO_2$) (Tokyo, Japan). A seed dose was $2 \times 10^5$ cells/ml in the starting inoculum or $2 \times 10^4$ cells/well. Herpes Simplex viruses were cultured under the same conditions in the MEM medium without serum (maintenance medium). Starting viral titers were $10^7$ $TCID_{50}$/ml.

For DMSO-soluble preparations, stock solutions were prepared in a concentration of 10 mM in DMSO. For water-soluble preparations, a stock solution prepared had the same concentration in the MEM medium (Minimal Essential Medium) for cell cultures. To control cytotoxicity (see below), the stock solution was diluted in the medium to a concentration of 100 μM and ten-fold serial dilutions of the preparations were made in the MEM medium (for DMSO-soluble compounds—in the MEM medium comprising 3% DMSO). The following concentrations of the preparations were used in the study of antibacterial action: if toxicity was not found, the concentrations of 100 μM preparations were 100, 10 and 1 μM; if toxicity was detected, the concentrations of 100 μM preparations were 10, 1, and 0.1 μM.

Acyclovir (10 μg/ml) was used for Herpes Simplex viruses of both types as a reference preparation to control the viral model validity.

To study antiviral activity, plate wells with a cell monolayer were added with the preparations in an amount of 0.1 ml/well. To compensate a reduction in the concentration of the preparations, which takes place in the following addition of viruses, twofold concentrations of compounds (i.e. 200, 20 and 2 or 20, 2 and 0.2 μM for toxic and non-toxic concentrations of 100 μM preparations, respectively) were used, incubated for an hour and then were infected with the examined 0.1 ml/well viruses in doses 1, 10 and 100 $TCID_{50}$ (50% tissue infectious dose).

The infected cells were incubated (37° C., 5% $CO_2$) for 48 hours and the monolayer condition was evaluated under a Leica DMIL HC microscope taking into account the nature of cytopathogenic action, which significantly differ for a virus, and the action of a preparation in its toxic concentration. The virus-specific cytogenic action was manifested in an increase in the size of cells, their rounding, and detachment from a substrate. These morphological characteristics served as their marked difference from the cells subjected to a toxic action of high concentrations of the examined preparations. The latter acquired spindle-like shape, lost contacts with neighboring cells of the monolayer, and their boundaries became more distinct.

Intensity of the virus-specific changes in the cells were semi-quantified using a 4-score system: 0—CPA (cytopathogenic action) is not detected; 1—up to 25% virus-infected monolayer; 2—from 25% to 50%; 3—from 50% to 75%; and 4—from 75% to 100%. The antiviral activity of a compound was evaluated according to their ability to reduce the manifestation of cytopathogenic action in the plate wells compared to the control values. Differences with the control values by 1 score and more were considered to be significant.

TABLE 5

Antiviral activity of the claimed compounds of general formula (I) against Herpes Simplex Virus type 1 and type 2: manifestation of the virus CPA (scores) in different concentrations of hemin derivatives, μM

| | Virus dose, lgEID 50 | | | | | | | | | | | |
|---|---|---|---|---|---|---|---|---|---|---|---|---|
| | 1 | | | | 10 | | | | 100 | | | |
| Concentration | 100 | 10 | 1 | 0.1 | 100 | 10 | 1 | 0.1 | 100 | 10 | 1 | 0.1 |
| Herpes Simplex Virus type 1 | | | | | | | | | | | | |
| IV | n/t | $0^1$ | 1 | 1 | n/t | $0^1$ | 2 | 2 | n/t | $2^1$ | 3 | 3 |
| VI | n/t | $0^1$ | $0^1$ | $0^1$ | n/t | 2 | 2 | 2 | n/t | 3 | 3.3 | 3 |
| Acyclovir, 10 μg/ml | | $0^1$ | | | | $0^1$ | | | | $0^1$ | | |
| Virus control without a preparation | | 1 | | | | 2 | | | | 3.3 | | |
| Herpes Simplex Virus type 2 | | | | | | | | | | | | |
| II | n/t | $0^1$ | 0.5 | 1 | n/t | $1^1$ | 2 | 1.5 | n/t | 3 | 3 | 3 |
| IV | n/t | $0^1$ | 0.5 | 1 | n/t | $0^1$ | 2 | 2 | n/t | $0^1$ | 3 | 3 |
| V | n/t | $0^1$ | 0.5 | 1 | n/t | $0^1$ | 2 | 2 | n/t | $2^1$ | 3 | 3 |
| VI | n/t | $0^1$ | 1 | 1 | n/t | $0^1$ | 2 | 2 | n/t | $2^1$ | 3 | 3 |
| IX | n/t | $0^1$ | 0.5 | 1 | n/t | $1^1$ | 2 | 2 | n/t | 3 | 3 | 3 |
| X | n/t | $0^1$ | 1 | 1 | n/t | 1.5 | 2 | 2 | n/t | 3 | 3 | 3 |
| XII | n/t | $0^1$ | 0.5 | 0.5 | n/t | $1^1$ | 1.5 | 2 | n/t | 3 | 3 | 3 |
| XIII | n/t | 0.5 | 1 | 1 | n/t | $1^1$ | 2 | 2 | n/t | 3 | 3 | 3 |
| Acyclovir, 10 μg/ml | | $0^1$ | | | | $0^1$ | | | | $0^1$ | | |
| Virus control without a preparation | | 1 | | | | 2 | | | | 3 | | |

[1] differences from the control wells without a preparation: reduction in CPA manifestation by 1 core or more.

As can be seen from Table 5, most examined claimed compounds were active against Herpes Simplex Virus type 1 in sub- and micromolar concentrations.

Example 23

Toxicity of the Novel Compounds

The novel compounds are substantially non-toxic; 1-5% death of leukocytes was observed for concentrations of from 12 to 50 μM.

The examined novel compounds also did not cause a significant hemoglobin release from erythrocytes of human blood (the observed release was not more than 2-3% for concentrations of up to 50 μM).

The obtained results testify the potential of the claimed compounds to be used for manufacture of non-toxic biocompatible antibacterial and antiviral agents based thereon as well as for the prevention and treatment of diseases caused by various microorganisms.

Thus, compared to the known compounds [RU patent No. 2415868 C1, published on Apr. 10, 2011; RU patent 2404191 C2, published on Nov. 20, 2010], the claimed compounds are characterized by a high water-solubility, antibacterial activity exhibited in lower concentrations, against both gram-positive and gram-negative resistant bacterial strains, and antiviral activity against Herpes Simplex Virus type 1 and type 2, which increases their potential and practice values as anti-infectious agents.

Example 24

The compositions according to the present invention can be used as disinfecting, antiseptic and pharmaceutical preparations (for example, in solid, semi-solid or liquid forms) comprising the proposed claimed compounds as an active agent, in a combination with organic or non-organic carriers or excipients suitable for intramuscular, intravenous, intranasal, oral, sublingual, inhalation and intrarectal administrations. The active agent can be introduced into the composition together with traditionally used nontoxic pharmaceutically acceptable carriers, suitable for the manufacture of solutions, tablets, pills, capsules, suppositories, emulsions, suspensions, sprays, inhalers, drops, ointments, or other drug dosage forms. Carriers can be water, glucose, lactose, gum arabic, gelatin, starch, magnesium trixylitol, talc, cornstarch, urea, polyethylene glycol, and other carriers suitable for manufacturing solid, soft, or liquid preparations. Herein, stabilizers, thickeners, coloring agents and flavoring agents may be used as additives.

A compound of general formula (I) is contained in the composition in an amount sufficient for providing an expected antibacterial and/or antiviral effect.

In manufacturing a unit dosage form, the amount of the active agent formulated with a carrier can be varied depending on the recipient under the therapy and on the particular route of administration of the therapeutic agent.

For example, when compounds of the present invention are used as solutions for injection, the content of the active agent in the solution ranges from 0.001 to 1% by weight. Diluents for the compounds can be 0.9% sodium chloride solution, distilled water, Novocain solution for injections, Ringer's solution, and glucose solution. When compounds of general formula (I) are used as tablets or suppositories, the amount of the compound ranges from 1.0 to 100.0 mg per unit dosage form. For tablets and suppositories, the pharmaceutical excipient can be any pharmaceutically suitable base.

Example Dosage

A. Gelatin Capsules

The powder to be introduced into capsules is formulated as follows:

| | |
|---|---|
| A compound corresponding to the general formula (I) | 1 to 50 mg |
| Magnesium oxide | 50 mg |
| Starch | 100 to 200 mg |

The above-listed ingredients are blended, and the blend is introduced into hard gelatin capsules in an amount of from 151 to 285 mg.

B. Tablet Dosage Form

A tablet dosage form is manufactured using the ingredients listed below:

| | |
|---|---|
| A compound corresponding to the general formula (I) | 1 to 50 mg |
| Potato starch | 100 mg |
| Polyvinylpyrrolidone | 10 mg |
| Magnesium stearate | 2 mg |
| Lactose | 48 to 82 mg |
| Aerosil | 5 mg |

The components are blended and compacted to produce tables each weighing 200 mg.

C. Aerosol Dosage Form

An aerosol blend intended for 10-time administration is formulated as follows:

| | |
|---|---|
| A compound corresponding to the general formula (I) | 10 to 100 mg |
| Magnesium oxide | 150 mg |
| Lactose | 110 to 140 mg |

The compound is blended with excipients, and the blend is transferred into a special spraying device.

D. Suppositories

The following suppository bases can be used:
water-insoluble bases (cocoa butter);
water-soluble or water-miscible bases (gelatin-glycerol or polyethylene oxide); and
combination (soap-glycerol) bases.
An example suppository formulation:
A compound corresponding to the general formula (I) in an amount of 1 to 50 mg, and cocoa butter in an amount necessary for a suppository to be obtained.
When necessary, rectal, vaginal, or urethral suppositories with appropriate excipients can be manufactured.

E. Ointments

The following ointment bases can be used:
hydrocarbon ointment bases, such as white Vaseline and yellow Vaseline (Vaselinum album and Vaselinum flavum, respectively), Vaseline oil (Oleum Vaselini), and white ointment and liquid ointment (Unguentum album and Unguentum flavum, respectively), with thickening additives such as solid paraffin and wax;

absorptive ointment bases, such as hydrophilic Vaseline (Vaselinum hydrophylicum), lanoline (Lanolinum), and cold cream (Unguentum leniens);

water-removable ointment bases, such as hydrophilic ointment (Unguentum hydrophylum); water-soluble ointment bases, such as polyethylene glycol ointment (Unguentum Glycolis Polyaethyleni); bentonite bases; and others.

An example ointment formulation:

| | |
|---|---|
| A compound corresponding to the general formula (I) | 0.01 to 0.1 g |
| Vaseline | 10 g |

Ointments are prepared by the proper technologies.

E. Solution for Injections

The solvents useful to prepare solutions for injection include 0.9% sodium chloride solution, distilled water, and Novocain solution. Unit dosage forms may be manufactured as ampoules, vials, and ampins.

The formulation of the solution for injection is as follows:

| | |
|---|---|
| A compound corresponding to the general formula (I) | 1 to 50 mg |
| Distilled water | 1 to 2 ml |

Injection dosage forms may be manufactured as sterile solutions, sterile powders, and sterile tablets.

Example Formulations for Disinfectant and Antiseptic Agents

F. Example of a Formulation

| | |
|---|---|
| A compound corresponding to the general formula (I) | 0.001 to 1% |
| 1-Propanol | 30 to 40% |
| 2-Propanol | 10 to 70% |
| Distilled water | 10 to 60% |

G. Example of a Formulation

| | |
|---|---|
| A compound corresponding to the general formula (I) | 0.001 to 1% |
| A quaternary ammonium base (or a mixture thereof) | 2 to 10% |
| Distilled water | to 100% |

H. Example of a Formulation

| | |
|---|---|
| A compound corresponding to the general formula (I) | 0.001 to 1% |
| Dimethyl sulfoxide (DMSO) | 1 to 20% |
| Or polyethylene glycol (PEG) with MM = 200 to 12000 | 1 to 20% |
| Distilled water | to 100% |

I. Example of a Formulation

| | |
|---|---|
| A compound corresponding to the general formula (I) | 0.001 to 1% |
| A mixture of alcohols, DMSO, PEG, and surfactants in various combinations and proportions | 1 to 80% |
| Distilled water | to 100% |

J. Example of a Formulation

| | |
|---|---|
| A compound corresponding to the general formula (I) | 0.001 to 1% |
| Distilled water | to 100% |

Thus, hemin derivatives of general formula (I) as claimed in the present invention have an increased water-solubility, antibacterial (including against resistant bacterial strains) and antiviral activities (including herpes viruses). Further, among the novel hemin derivatives there have been revealed the hemin derivatives active against gram-positive bacterial strains. The efficacy of separate members of the novel compounds of general formula (I) proves their suitability for the use in formulations of disinfectant, antiseptic, and therapeutic agents having an antibacterial and/or antiviral action.

The invention claimed is:
1. A compound of formula (I)

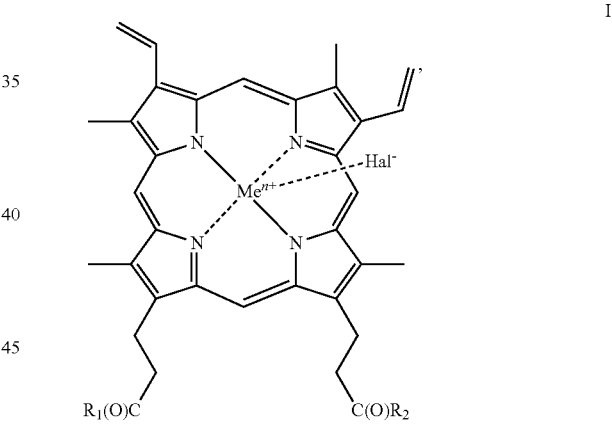

wherein $R_1$ is selected from the group consisting of

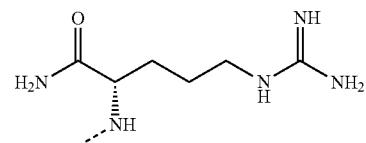

ArgNH$_2$

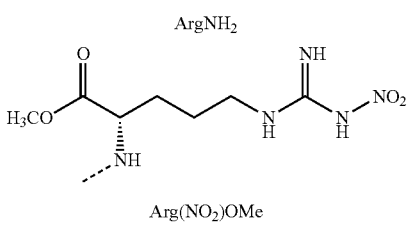

Arg(NO$_2$)OMe

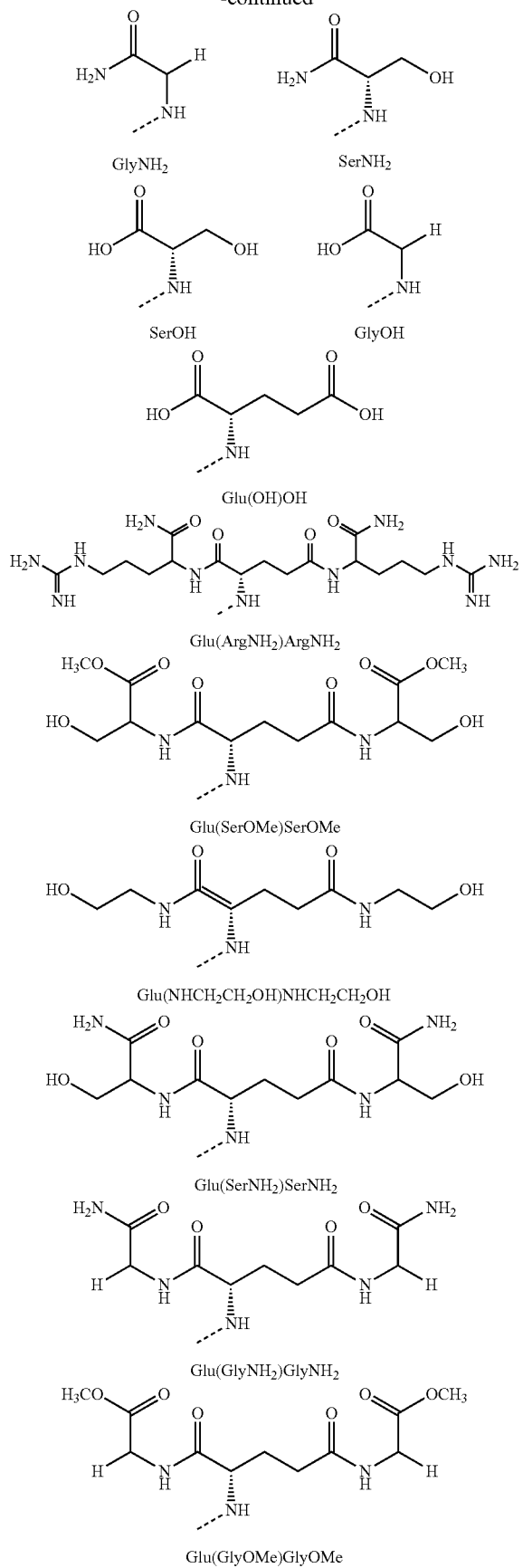
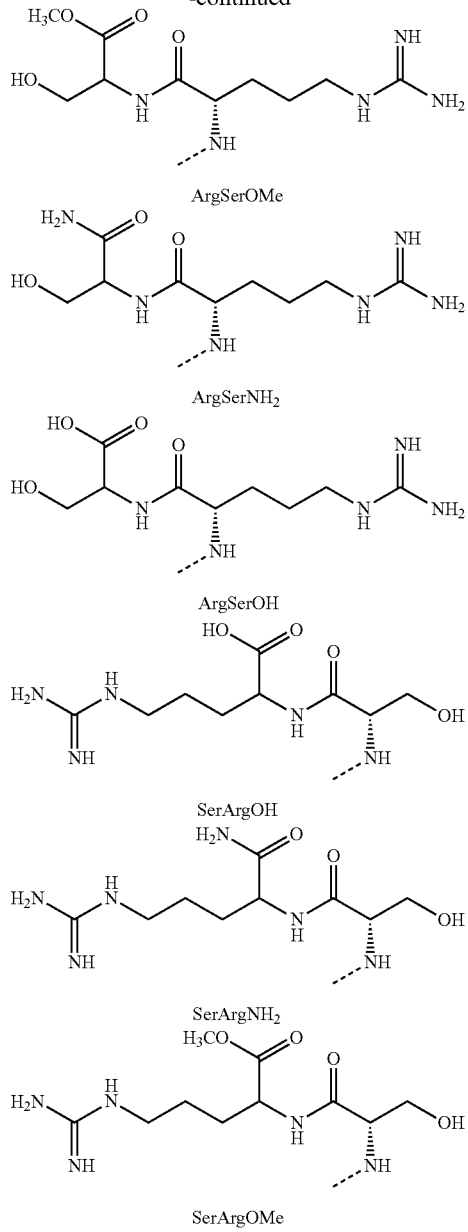

$R_2$ is the same as $R_1$;
$Me^{n+}$ is $Fe^{2+}$ or $Fe^{3+}$; $Hal^-$ is $F^-$, $Cl^-$, $Br^-$ or $I^-$,
or a pharmaceutically acceptable salt thereof.

2. The compound or a salt thereof according to claim 1, wherein both $R_1$ and $R_2$ are $ArgNH_2$, $GlyNH_2$, $SerNH_2$, $Glu(ArgNH_2)ArgNH_2$, $Glu(SerNH_2)SerNH_2$, $Glu(GlyNH_2)GlyNH_2$, $ArgSerNH_2$, or $SerArgNH_2$.

3. The compound or a salt thereof according to claim 1, wherein both $R_1$ and $R_2$ are SerOH, GlyOH, Glu(OH)OH, ArgSerOH, or SerArgOH.

4. The compound or a salt thereof according to claim 1, wherein both $R_1$ and $R_2$ are $Glu(NHCH_2CH_2OH)NHCH_2CH_2OH$, Glu(GlyOMe)GlyOMe, ArgSerOMe, or SerArgOMe.

5. A pharmaceutical composition having an antibacterial and/or antiviral activity, which comprises as an active agent a compound of formula (I) or a pharmaceutically acceptable salt thereof according to claim 1, the pharmaceutical composition further comprising a pharmaceutically acceptable carrier or excipient.

6. A pharmaceutical composition having an antibacterial and/or antiviral activity, which comprises as an active agent a compound of formula (I) or a pharmaceutically acceptable salt thereof according to claim 2, the composition further comprising a pharmaceutically acceptable carrier or excipient.

7. A pharmaceutical composition having an antibacterial and/or antiviral activity, which comprises as an active agent a compound of formula (I) or a pharmaceutically acceptable salt thereof according to claim 3, the composition further comprising a pharmaceutically acceptable carrier or excipient.

8. A pharmaceutical composition having an antibacterial and/or antiviral activity, which comprises as an active agent a compound of formula (I) or a pharmaceutically acceptable salt thereof according to claim 4, the composition further comprising a pharmaceutically acceptable carrier or excipient.

9. The pharmaceutical composition according to claim 5, which is active against Gram-positive *Staphylococcus, Enterococcus, Micrococcus* and/or *Escherichia* genera.

10. The pharmaceutical composition according to claim 9, which is active against Gram-positive *Staphylococcus aureus, Enterococcus faecalis, Micrococcus luteus, Staphylococcus epidermidis, Enterococcus faecium* species, or against gram-negative *Escherichia coli*.

11. The pharmaceutical composition according to claim 10, wherein the Gram-positive bacteria are the *Staphylococcus aureus* 209P, *Enterococcus faecalis* BKM B-871, *Micrococcus luteus* BKM Ac-2230, *Staphylococcus aureus* No. 25923 ATCC, *Staphylococcus aureus* No. 100 KC, *Staphylococcus aureus* No. 5 MRSA, *Staphylococcus aureus* No. 3797 MRSA, *Staphylococcus epidermidis* No. 533, *Enterococcus faecalis* No. 559, *Enterococcus faecium* No. 569 or gram-negative *Escherichia coli* 4300 strain.

12. The pharmaceutical composition according to claim 5 which is active against Herpes virus.

13. The pharmaceutical composition according to claim 12, which is active against Herpes Simplex Virus type 1 and/or type 2.

14. The pharmaceutical composition according to claim 12, which is active against the Herpes Simplex Virus type 1 EC strain and type 2 G strain (ATCC No. VR-734).

\* \* \* \* \*